United States Patent [19]

Askham

[11] Patent Number: 5,296,226
[45] Date of Patent: Mar. 22, 1994

[54] BIRD REPELLENT COMPOSITIONS

[75] Inventor: Leonard R. Askham, Pullman, Wash.

[73] Assignee: Dolphin Trust, Pullman, Wash.

[21] Appl. No.: 954,952

[22] Filed: Sep. 29, 1992

Related U.S. Application Data

[63] Continuation-in-part of Ser. No. 654,960, Feb. 12, 1991, abandoned, and a continuation-in-part of Ser. No. 781,375, Oct. 23, 1991, abandoned.

[51] Int. Cl.$^5$ .............................................. A61K 9/107
[52] U.S. Cl. ................................... 424/405; 514/537; 514/943
[58] Field of Search ...................... 424/405, 84, 943; 514/537

[56] References Cited

U.S. PATENT DOCUMENTS

| | | | |
|---|---|---|---|
| 2,967,128 | 1/1961 | Kare | 167/46 |
| 3,171,231 | 3/1965 | Forrest | 47/2 |
| 3,533,810 | 10/1970 | Shillington et al. | 106/15 |
| 4,693,889 | 9/1987 | Chirchirillo et al. | 424/83 |
| 4,790,990 | 12/1988 | Mason et al. | 424/438 |
| 4,806,151 | 2/1989 | Bohus et al. | 71/111 |
| 4,870,102 | 9/1989 | Puritch et al. | 514/493 |
| 4,873,082 | 10/1989 | Cacioli et al. | 424/83 |

OTHER PUBLICATIONS

Puritch, George S., "Biocidal Effects of Fatty Acid Salts on Various Forest Insect Pests," Chapter 10, 105–112. (Publication name and date unknown).

Puritch et al., "Effect of Insectidal Soap Used in the Gypsy Moth Control Program in Kitsilano on Insects and Vegetation," Canadian Forestry Service, Mar., 1981.

Puritch, "The Toxic Effects of Fatty Acids and Their Salts on the Balsam Woolly Aphid, Adelges piceae (Ratz.)," Canadian J. For. Res. 5, 515–522 (1975).

Thomas, Gareth J., "Herbicidal Activity of 6-Methylanthranilic Acid and Analogues," J. Agric. Food Chem., 1984, 32, 747–749.

Cummings, J. L., J. R. Mason, D. L. Otis and J. E. Davis, Jr., "Executive Summary," USDA/Aphis-/ADC, 1991.

Hellman, Edward W., et al., "Preliminary Evaluation of Dimethyl Anthranilate as a Bird Repellent on Grapes," Am. J. Enol. Vitic., 40(2):140–142 (1989).

Mason, J. R. et al., "Behavioral Assessment of Olfactory and Trigeminal Responsiveness of Starlings *Sturnus vulgaris* to Nine Anthranilates," Abstract, (No source or page number, no date).

Mason, J. R. et al., "Anthranilate Repellency to Starlings: Chemical Correlates and Sensory Perception," J. Wildl. Manage, 53(1):55–64 (1989).

Mason, J. R. et al., "Evaluation of Dimethyl Anthranilate as a Non-Toxic Starling Repellent for Feedlot Settings," Proceedings, First Eastern Wildlife Damage Control Conf., Cornell Univ., Ithica, N.Y., Sep., 27–30 (1983).

Mason, J. R. et al., "Field Evaluation of Dimethyl Anthranilate as a Bird Repellent Livestock Feed Additive," J. Wild. Manage. 49(3): 636–642 (1985).

(List continued on next page.)

*Primary Examiner*—Thurman K. Page
*Assistant Examiner*—Raj Bawa
*Attorney, Agent, or Firm*—Wells, St. John, Roberts, Gregory & Matkin

[57] ABSTRACT

A composition for reducing phytotoxicity of benzoic derivatives of esters of phenyl acetic acid or dimethyl benzyl carbonyl acetate is formed by combining the repellent in an aqueous solution with a an anionic surfactant or emulsifier, such as a salt of a fatty acid. The resulting solution can be applied to surfaces of bird edible materials that are to be protected from bird depredation or utilized directly in an associated water system. The solution forms a film on the surfaces of the bird edible materials. The resulting film reduces the normal degradation of the repellent when exposed to sunlight and its phytotoxicity.

6 Claims, 4 Drawing Sheets

OTHER PUBLICATIONS

Bean, N. J. et al., "Dimethyl Anthranilate Repellency to Mallard Ducks (*Anas platyrhynchos*) and Ring-Necked Pheasants (*Phasianus colchicus*)," Internal document given to inventor by the authors, 1987.

Glahn, J. F. et al., "Dimethyl Anthranilate as a Bird Repellent in Livestock Feed," Wildl. Soc. Bull., 17:313–320 (1989).

Askham, Leonard R. et al., "The Use of DMA to Reduce Robin Depredation on Cherries," Proceedings: 9th Great Plains Wildlife Damage Control Workship, Fort Collins, Col., 116–119, Apr. 17–20, 1989.

Avery, Michael L. et al., "Evaluation of Methyl Anthranilate for Reducing Bird Damage to Fruit Crops," U.S. Dept. of Agriculture, Bird Damage Research Report No. 447, Dec. 1989.

Avery, Michael L., "Flight Pen Evaluation of Methyl Anthranilate Formulations for Reducing Bird Damage to Blueberries," Denver Wildlife Research Center Bird Section Research Report No. 471, Feb., 1991.

Askham, Leonard R., "Efficacy of Methyl Anthranilate as a Bird Repellent on Cherries, Blueberries and Grapes," 15th. Vertebrate Pest Management Conference, Newport Beach, Calif., Mar. 3–5, 1992.

BIRD REPELLENT COMPOSITIONS

RELATED APPLICATIONS

This is a continuation-in-part of pending patent applications Ser. No. 654,960, filed on Feb. 12, 1991, titled "Bird Repellent Compositions," which is now abandoned; and Ser. No. 781,375, filed on Oct. 23, 1991, titled "Bird Repellent Compositions", which is abandoned in favor of the present application.

TECHNICAL FIELD

This invention relates to a bird repellent composition for agricultural, aquatic, structural and other uses. It provides a formulation that makes a known bird repellent capable of being used in an aqueous solution for introduction to water-based systems used in crop-related applications and for directly coating outer surface areas of growing bird-edible materials and other animate and inaminate objects.

BACKGROUND OF THE INVENTION

The transmission of diseases and damage to man-made structures as well as crops by birds is well known and documented. Substances that are obnoxious, offensive, repugnant, revulsive or otherwise repulsive to birds have been known for a number of years. Some of these substances have been tried, with varying degrees of success, as bird repellents on assorted crops, feeds and surfaces.

U.S. Pat. No. 2,967,128 to Kare discloses a number of derivatives of anthranilic acid esters and esters of phenyl acetic acid which are proposed as taste repellents for birds. U.S. Pat. No. 4,790,990 to Mason et al. (which lists Kare as a coinventor) discloses a combination that encapsulates these repellents in starch matrices that are then added to livestock feed to reduce its consumption by birds.

The preferred repellents disclosed by Kare are water insoluble dimethyl anthranilate, methyl anthranilate, ethyl anthranilate, phenyl ethyl anthranilate, menthyl anthranilate, and dimethyl benzyl carbonyl acetate. Kare proposes the dispersal of these repellents by using organic solvents and liquid or solid carriers. The Mason et al. disclosure is directed to partial entrapment of the repellents in edible solid vehicles, such as modified food starches.

A number of serious problems have been encountered in attempted experiments following the disclosed information provided by the Kare patent. They would preclude the use and application of these repellents to agricultural crops. These include the continued insolubility of the active ingredients in water, their toxicity to plants (phytotoxicity), their extremely short life span under sunlight, and the attractiveness of these chemical agents to insects.

The insolubility of dimethyl and methyl anthranilate in water was the first major problem encountered. When combined with the solvents and synthetic surfactants described in the patent neither dimethyl or methyl anthranilate, the two most common anthranilic derivatives available for commercial use, remained soluble when mixed with water, which is the preferred medium for commercial applications of pesticides. Large quantities of one or two gallons of these pesticides were difficult to combine with two or four hundred gallons of water in commercial sprayers. The anthranilic oils would either separate into globules, form a film on the water surface, adhere to the walls of the metal tanks or destroy the plastic hoses. Precipitates quickly formed once agitation was stopped and were difficult to reincorporate into the water. When applied to a crop, spots of anthranilic oil were left on the plant surfaces rather than forming an even protective coating.

Plant toxicity (phytotoxicity) with both dimethyl and methyl anthranilate were immediately noted in experimental efforts using materials and techniques that followed the Kare disclosures. This is not in itself surprising, since these chemicals have recognized herbicidal properties. Brown spots appeared within twenty minutes after application where either of the anthranilates touched the leaf or fruit surfaces at 2500 parts per million (ppm) concentration rates. All of the leaves and plants on the plants immediately turned brown when the application rate was doubled. Tests conducted to determine the upper ranges of phytotoxicity indicated that the concentration limits for the repellents were far below that needed to repel birds from the tested crops.

The efficacy of both dimethyl and methyl anthranilate in reducing bird depredation of crops, as described by Kare, was also observed to be limited. Birds, when observed in confinement and in the field, readily returned to the crop or food source on the fourth day after application. It was hypothesized that the characteristic odor or flavor, associated with either compound, was not detected by the birds.

A series of tests were developed to prove this theory. In the first experiment, conducted under laboratory conditions, the results indicated that the compounds decompose within sixty-four hours when exposed to ultraviolet light. Moreover, the addition of solvents increased the volatility of the anthranilates and, in some cases, may have contributed to the phytotoxic properties. Some organic solvents can also be toxic to humans and animals feeding on the harvested treated crops.

In an experiment designed to separate the effects of ultraviolet light from the light spectrum and to assess its impact on the anthranilates, a series of petri dishes containing either methyl anthranilate or methyl anthranilate combined with potassium salts of fatty acids were placed in the out-of-doors. The results showed unequivocally that ultraviolet light is the primary factor that causes the methyl anthranilate to lose its primary odor and taste repellent properties.

The research leading to this disclosure showed that the addition of anionic surfactants or emulsifiers, such as alkyl metal salts of fatty acids or naturally occurring soaps, alleviates this problem of low solubility in water. This is accomplished by forming a consistent emulsion that suspends the repellent in an aqueous solution without separation or precipitation during the application process.

By combining them with natural soaps, the acceptable upper range of concentration of the active repellents was increased by a factor of 15 to 65 on the plants tested. Furthermore this addition greatly extended the life of the repellent properties of the compositions by 150%, to a total of ten days.

The use of encapsulation, as disclosed by the Mason et al. patent, was explored but discarded. Encapsulation eliminates volatility, an important discovery of this patent disclosure. It also precludes the adhesion of either dimethyl or methyl anthranilate directly to the surface of the object to be protected unless additional adhesive agents are added to the formulation. Use of adhesive agents is an alternative which is cost prohibitive for commercial applications of these repellents.

In experiments developed to determine the response of birds to dimethyl and methyl anthranilate treated fruits, grains, water, perches and nests it was discovered that the fragrances or aromas may be more repulsive than taste. Birds presented with both treated and untreated fruits, grains and water for the first time initially fed or drank from both for a short period, generally less than two minutes, before abandoning the treated samples. When reintroduced in reverse order the birds refused to touch the treated materials even though they had not fed or drank from the containers for several hours. The addition of untreated food on suspended screens above the treated materials, elicited the same results. No foods were eaten as long as the anthranilic odors could be detected by the birds. Birds would also not return to perches treated with the compounds until the odor of the active repellents had dissipated.

It was also discovered that insects are readily attracted to dimethyl and methyl anthranilate. Crops relatively free of insects were quickly reinfested after being treated with either material. The addition of soaps, however, reduced this problem.

Bird repellents designed to reduce depredation over a large area must be applied in an aqueous medium with power assisted equipment. Dimethyl and methyl anthranilate, to this point, have required that they be solubilized with organic solvents and emulsifiers or surfactants before they are placed in an aqueous medium. This, in turn, has created further dispensing problems. Distribution is difficult because the repellents agglomerate as globules or precipitate within the aqueous medium used as the dispensing agent. The resulting concentration of the repellent leaves an uneven layer of repellent on treated surfaces and can discolor, burn and kill treated plants. Experimental treatments of dimethyl and methyl anthranilates on cherries, blueberries and grapes, resulted in spotty coverage and serious plant injury. The repellents attracted unwanted insects and required repeated applications every four to five days to be effective. Application with the unique formulations, herein described, greatly enhanced the repellency characteristics of the anthranilates.

This invention discloses a novel formulation that eliminates or reduces the above described problems. The combination of materials disclosed herein produces a uniform application solution, extends the useful life of the repellent, eliminates plant phytotoxicity within prescribed application rates, and reduces insect reinfestations.

The use of certain fatty acids as biodegradable insecticides is well-known in the literature. For example, U.S. Pat. No. 4,870,102 to Puritch et al. describes a composition and method of killing mites with a mixture of salts of fatty acids and alcohol.

BRIEF DESCRIPTION OF THE DRAWINGS AND TABLES

The embodiment of the invention is illustrated in the accompanying tables and figures.

Table 1 is a summary of results from combining different surfactants, emulsifiers and salts of fatty acids with dimethyl and methyl anthranilates, at the same volume to volume ratios, and then added to water.

Table 2 is a summary of the results obtained when Tween, Regulaid and potassium salts of fatty acids are combined with methyl anthranilate, mixed with water, applied to living plant tissue at increasingly higher concentrations, and compared with the emulsifiers and untreated water as controls to determine phytotoxic thresholds.

DETAILED DESCRIPTION OF THE PREFERRED EMBODIMENTS

Figure 1:
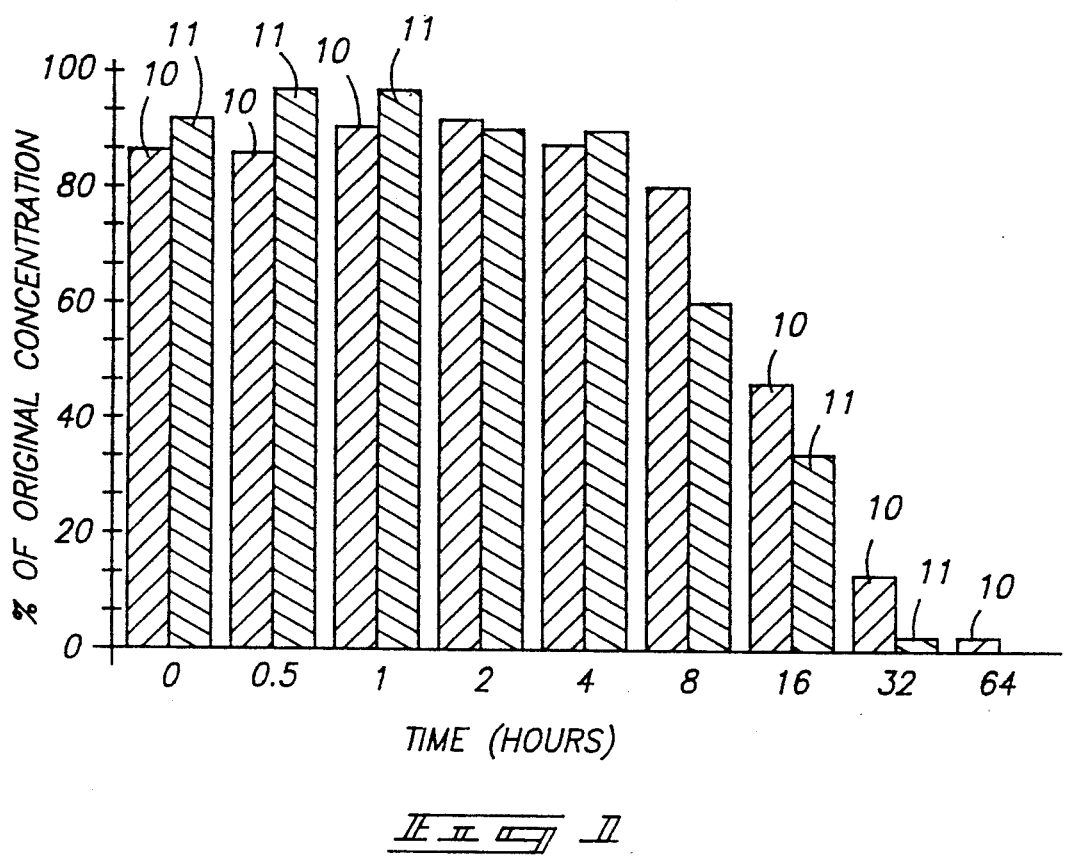
FIG. 1 is a plot of test results showing the effect of fluorescent, incandescent and ultraviolet light on methyl anthranilate and methyl anthranilate mixed with Tween (20) in a controlled environment chamber.

The following disclosure of the invention is submitted in furtherance of the constitutional purpose of the Patent Laws "to promote the progress of science and useful arts" (Article 1, Section 8).

The avian repellent formulation of this invention consists of a mixture of one or more of the previously known chemical repellent compounds combined with one or more mixtures of an anionic surfactant or emulsifier, such as salts of certain fatty acids. The invention uses two naturally occurring ingredients that, when combined, become an odor and taste aversive agent in reducing avian depredation of agricultural crops or bird edibles and other surfaces.

The first component is one or more of a mixture of chemical compounds which have repellent affects, through smell and taste, on birds. The repellent compounds are, in general, benzoic derivatives of esters of anthranilic acids, esters of phenylacetic acid, or dimethyl benzyl carbonyl acetate all hereinafter referred to as "repellents." The active ingredient includes those disclosed in U.S. Pat. No. 2,967,128 to Kare, which is incorporated into this disclosure by reference, as well as any other benzene derivatives with similar repellent properties.

The second component is one or more of a mixture of chemical compounds which form micelles with the first component to achieve uniform aqueous emulsions and even lamellar distribution over an applied surface. More specifically, the second component is one or more anionic surfactants or emulsifiers, such as the alkali metal salts of saturated and/or unsaturated fatty acids. They are often called "natural soaps." Included, but not limited within these compounds are various anionic surfactants and emulsifying agents including metal salts of fatty acids.

Methyl and dimethyl anthranilate, along with fifty-four of their 6-methyl anthranilic acid analogs, are known herbicidal agents. The principal mode of action is hypothesized to cause initial erosion of the surfaces, waxes and cutin layers, where they enter the plant through the interspacial pores of the epidermal cell walls as well as through stomatal pores and guard cells.

The exact method by which anthranilates act as herbicidal agents, however, is unclear. It is known that aromatic ring compounds tend to adsorb preferentially to aliphatic surfaces such as the waxy coatings commonly found on fruit and vegetation. Further that the less soluble a material the more strongly it will tend to be adsorbed to these surfaces.

Living organisms, such as plants, are maintained at a constant positive pressure gradient between cells and between cells and the atmosphere. Low surface tension liquids, such as the anthranilates, have a positive initial spreading coefficient that suspends them on liquids, but a near zero or negative final surface tension when applied to a surface.

Benzene compounds, such as methyl and dimethyl anthranilate, produce a $-1.6$ pressure gradient along the surface to which they are applied. This negative osmotic potential reduces the intersurface tension to first erode the surface and then disrupt the inter-cellular water balance. The cell walls then rupture, causing the liquid to flow through the membranes. When the pressure gradient is extensive, fluids from the adjoining cells move through their respective cell walls until the gradient is again normalized or the region becomes desiccated.

It is also well known that certain surfactants increase the efficacy of some herbicidal agents. This is accomplished by either breaking down or eroding the waxes and cutin layers of the plant, as described above, reducing the intersurface tension between the plant surface and the solution, or both. When either or both of these activities occur, the epidermal cells of the plant are left exposed to the direct penetration of the herbicide. The phenomenon is very complicated and difficult to analyze or predict. The extent of adsorption of a surfactant and solute depends entirely on its chemical structure and on the solvent.

Nonionic, cationic and amphoteric solvents tend to reduce surface tension more than anionic solvents. As a result, solutes incorporated with the former three tend to come in contact more readily with the surface than solutes incorporated with anionic surfactants. Furthermore the less soluble a material the more strongly it will tend to be adsorbed to a surface with the former three than with an anionic surfactant.

When strongly adsorbing anions and cations are present in a suspension, the ions may interact at the surface in a number of ways. There may be favorable or unfavorable electrostatic interactions, the various ions may compete for available surface sites, or some of the ions may form bridges between the surface and other ions. Only when the anions form a new surface phase with the surface is cation adsorption affected significantly. Such a surface phase may form while the bulk solution is unsaturated.

As a result of the invention disclosed herein, it has been found that a bridge is formed by anionic surfactants, particularly alkyl metal salts of fatty acids with carbon chain lengths of 10 to 22, that separates slightly to insoluble oils in water and from surfaces to which they are applied.

The natural soaps of this formulation, unlike their synthetic counterparts, have been shown to form molecular micelles with the selected active repellent compounds. When added to water, an evenly distributed solution with no repellent precipitation, has been obtained. Upon application to a surface the micelles were found to form uniform platelike structures. Within each platelet one end of the molecule, with the repellent, orients toward the atmosphere while the other, containing the soap, orients toward the surface.

The carbon molecules of the natural soap protect the anthranilitic molecules from ultraviolet light exposure until the bond is broken by heat and surface air movements. Once the bond is broken the anthranilic molecules within each platelet become exposed, leaving succeeding layers of thin volatilizing anthranilate films that avian predators find objectionable. As the anthranilates volatilize into the atmosphere they dissipate until no detectable repellent residues remain on the treated surfaces.

As previously described, the application of anthranilitic derivatives are phytotoxic. The applicable literature pertaining to these compounds has reported on use of them as herbicidal agents. Phytotoxicity is reduced or eliminated with the combination of alkyl metal salts of fatty acids, to preclude direct contact of the anthranilates with the epidermal cells of plant tissues. By adding these salts of fatty acids to the active chemicals, the phytotoxic effects of dimethyl and methyl anthranilate were eliminated at proposed application rates of 2500 parts per million (ppm) to in excess of 90,000 ppm—far in excess of that needed to effect bird damage.

With these discoveries it was also found that the ratio between anthranilates and salts of fatty acids could be adjusted to develop formulations that were sensitive to individual plant phytotoxic thresholds and the length of time needed between application and harvest.

The preferred repellents, in the order listed, are methyl anthranilate and dimethyl anthranilate. Others may be substituted depending on availability and cost.

The salts of fatty acids are selected from the group of alkyl metal salts of saturated or unsaturated long chain fatty acids, wherein the chain length of the fatty acid is between 10 and 22 carbons inclusive; preferable 18 to 22. The alkyl metal salts are hydrogen, potassium, sodium, lithium, rubidium, cesium and francium. Included, but not limited to, are compounds within this broad category formulated with carboxylic acids (and salts thereof), phosphoric and polyphosphoric acid esters (and salts thereof), sulfonic acids (and salts thereof), sulfuric acid esters (and salts thereof), sulfated esters and sulfated natural fats and oils.

The preferred salts of fatty acids of this invention are derivatives of potassium and sodium. These salts of fatty acids may be either solid or liquid. They are typically diluted, either by the manufacturer or by the end user, to make an aqueous solution. Hydrogen, lithium, sodium, and potassium are readily available to plants in their natural environments. Rubidium and cesium are classified as rare elements. The process by which soaps and oils are combined to form emulsions in aqueous solutions and bind with surfaces is well known.

This novel formulation is prepared by combining the repellent ingredient with salts of fatty acids until an even composition is formed. The compositions of this invention may be formulated over a wide range of weight or volume ratios of the two components. Preferably, these ratios are in the range of 5:1 to 1:20 (repellent to fatty acid salt). The most preferred range is 1:1 to 1:4. The novel composition can then be diluted to the desired concentration, in an aqueous solution, and applied directly to the material, site, location or solution to be protected from birds. The preferable range of the final repellent aqueous solutions concentrations varies from 0.01% to 40% either by weight or volume. Typically, a concentrate of the two components is first formulated in the desired ratio. This can then be diluted and mixed with water or other carrier or dispersal agent by either the manufacturer or the end user to obtain the desired final concentration of both components.

The avian repellent compositions of this invention are applied to crops or other materials as an aqueous solution. They can be applied with liquid spray dispensers of any type or size. The repellent compositions can be applied by crop dusters or irrigation sprinklers, on a large scale, or by a portable liquid spray dispenser, for smaller scale applications. The avian repellent compositions may also be applied directly to bird's nests and roosts as a concentrate or dilution. The avian repellent composition can also be applied, as a concentrate, to aqueous solutions where bird use is not desired (such as impoundments and chemically treated irrigation systems.)

EXAMPLE 1

Tests showing the effect of emulsifying agents on methyl anthranilate

Fifteen solvents, emulsifiers, surfactants, oils, extenders and soaps were placed, in equal amounts, into a series of glass beakers, each of which contained the same amount of 99.9% methyl anthranilate. The mixtures were stirred for the same amount of time and a sub-sample withdrawn and placed in additional beakers, each containing the same amount of water, and agitated. Both sets of beakers were then placed at rest, and the results recorded (See Table 1).

In test 1 the methyl anthranilate quickly formed oil like droplets on top of the water in the beaker. In tests 2 and 3 the two solvents—ethanol and methanol—readily solubilized when added to methyl anthranilate, but quickly disassociated to form droplets with the water surface. In tests 4 through 7 Tween 20, Regulaid, Surf Ac 820 and Blendex readily formed even mixtures that remained consistent for twelve hours but precipitated out of the water in less than five minutes once agitation ceased. In tests 8 through 11 Peptol, Agridex, Activate 3 and Nufilm readily separated in less than five minutes and formed a precipitate in water in about the same amount of time. In test 9 Agri-dex not only separated but formed mildew-like white precipitates at the bottom of the beaker. When placed in water, a filmy yellow precipitate developed. In test 10 a distinct separation developed with the methyl anthranilate moving to the bottom leaving a frothy milky white substance on top. The mixture could not be remixed and no attempts to place it with the water was attempted. In test 11 the methyl anthranilate readily separated to the top of the Nufilm in less than 5 minutes and produced an oil film when placed in water. In test 12 Liqui-nox detergent produced an even milky white solution that separated in less than 10 minutes and left a milky white precipitate in the beaker with the water. In test 13 Blendex produced an uneven solution that separated in less than ten minutes. A filmy white precipitate, with some oil beads forming at the top of the water column, were observed within 30 minutes after agitation. In test 14 Norfox KO or potassium oleate developed a heavy yellowish paste that did not change in twelve hours. A good, even solution was obtained when placed in water. In test 15 Safer Insecticidal Soap produced a good, even clear amber solution that remained in solution when placed in water. In test 16 the potassium salts of fatty acids produced an even milky white solution that remained in solution when placed in water.

TABLE 1

Evaluation of combining emulsifiers, surfactants and potassium salts of fatty acids with methyl anthranilate and added to water.

| Test No. | Trade Name | Chemical Name | Time in solution (Min) | Comments | Time in Water Solution (min) | Comments |
| --- | --- | --- | --- | --- | --- | --- |
| 1 | | Methyl anthranilate | | | 0 | Oil beads on top of water. |
| 2 | | Ethinol | 720 | Even solution | 0 | Oil droplets formed immediately on top of water |
| 3 | | Methinol | 720 | Even solution | 0 | Same as 1 and 2 |
| 4 | Tween 20 | Polyoxyethylene (20) surbatin monolaurate | 720 | Even amber solution | >5 | Chalky white powder and bead precipitates |
| 5 | Regulaid | Polyoxyethylene-polypropoxy-propanol, dihydroxy-propane, Alkyl 2-ethyloxyethanol | 720 | Even clear to amber solution | >5 | Yellowish film precipitate |
| 6 | Surf Ac 820 | Sulfonated oil | 720 | Even mixture | >5 | Whiteish powdery precipitate |
| 7 | Blendex | Sodium salts of organic sulfonates and alcohol (64%) | 720 | Even mixture | >5 | Same as No. 6 |
| 8 | Peptoil | Paraphin based patrolium oil (83%) Surfactant blend (17%) | >5 | Uneven mixture. Distinct separation | 0 | 1/32 to ¼" oil beads at water surface. |
| 9 | Agri-dex | Paraphin based petrolium oil (99%) Adjuvant (1%) | >5 | Distinct separation with mildew like feathery white masses at bottom of beaker | >5 | Filmy yellow precipitate |
| 10 | Activate 3 | Dimethyl-polysiloxane (1%) Alkyl Oxy Polyethoxy Ethanol (9%) Propylene glycol (2%) Inactive (88%) | >5 | Distinct separation. Milky white on top, yellow on bottom | 0 | Would not remix. |
| 11 | Nufilm | di-1-p-Menthane (96%) | 0 | Oil separation | 0 | Oil separation to |

TABLE 1-continued

Evaluation of combining emulsifiers, surfactants and potassium salts of fatty acids with methyl anthranilate and added to water.

| Test No. | Trade Name | Chemical Name | Time in solution (Min) | Comments | Time in Water Solution (min) | Comments |
|---|---|---|---|---|---|---|
| | | Inerts (4%) | | to top of solution | | top of solution |
| 12 | Liqui-nox detergent | None listed | >10 | Heavy white mixture | >5 | Filmy white precipitate |
| 13 | Blencex | Potassium salts of complex organic sulfonates (64%) Adjuvants (36%) | 0 | Uneven separation throughout mixture | 0 | Filmy white precipitate with some oil droplets at bottom of beaker. |
| 14 | Norfox KO | Potassium oleate | 720 | Heavy yellow paste | 0 | Unable to mix with water |
| 15 | Safer Insectacidal Soap | Potassium salts of fatty acids (50%) Alcohol (30%) Inerts & builders (20%) | 720 | Light yellow solution. | 720 | No precipitates. Good even solution |
| 16 | | Potassium salts of fatty acids (30%) Inerts and builders (70%) | 720 | Milky white solution | 720 | No precipitates. Good even solution. |

The test results listed in Table 1 show that the solvents and surfactants disclosed by Kare, when combined with methyl anthranilate, are not soluble or emulsifiable when placed in water. These tests also show that natural soaps, when combined with methyl anthranilate, form an even emulsion that retains its integrity upon the termination of agitation.

EXAMPLE 2

Tests showing the effect of incorporating natural soaps with dimethyl and methyl anthranilate in reducing or eliminating plant phytotoxicity The leaves and maturing fruit of cherry, blueberry, grape and raspberry plants were selected for this study. Three sets of solutions were prepared by combining "Tween", "Regulaid" and potassium salts of fatty acids (soap) as emulsifiers with dimethyl and methyl anthranilate. Each set of concentrations contained either 0.13, 0.25, 0.50, 1.00, 2.00, 4.00, 8.00, or 16.00% by volume of the repellent material mixed with the emulsifier and added to water. Two solutions containing either water or the emulsifiers without the repellent were prepared as controls. The leaves of one branch from each plant were immersed in each solution and observed twenty-four hours post-treatment.

The results (See Table 2) show that neither the water or emulsifiers, when applied without the repellent compound, caused any damage to the plants. The leaves and fruit of cherries and blueberries did not show any signs of damage at the 0.13 and 0.25% concentration rates but were severely burned with anything over 0.5% when subjected to methyl anthranilate mixed with either Tween or Regulaid. Damage was readily apparent with both of these combinations on grapes and raspberries. Plant damage was not detected in any of the species when methyl anthranilate was combined with potassium salts of fatty acids and applied at 4.0% or less. Some discoloration, but no damage, was noted with 8.0 and 16.00% concentrations applied to any of the four plant species.

TABLE 2

The effect of Tween, Regulaid and potassium salts of fatty acids as an emulsifier with methyl anthranilate on plant damage.

| Emulsifier/Species | Water | Emulsifier | Phytoxicity Rating* Concentration (% active ingredient) | | | | | | | |
|---|---|---|---|---|---|---|---|---|---|---|
| | | | 0.13 | 0.25 | 0.5 | 1.0 | 2.0 | 4.0 | 8.0 | 16.00 |
| Tween | | | | | | | | | | |
| Cherries | 0 | 0 | 0 | 0 | 10 | 10 | 10 | 10 | 10 | 10 |
| Blueberries | 0 | 0 | 0 | 0 | 10 | 10 | 10 | 10 | 10 | 10 |
| Grapes | 0 | 0 | 5 | 10 | 10 | 10 | 10 | 10 | 10 | 10 |
| Raspberries | 0 | 0 | 10 | 10 | 10 | 10 | 10 | 10 | 10 | 10 |
| Regulaid | | | | | | | | | | |
| Cherries | 0 | 0 | 0 | 0 | 10 | 10 | 10 | 10 | 10 | 10 |
| Blueberries | 0 | 0 | 0 | 0 | 10 | 10 | 10 | 10 | 10 | 10 |
| Grapes | 0 | 0 | 5 | 10 | 10 | 10 | 10 | 10 | 10 | 10 |
| Raspberries | 0 | 0 | 10 | 10 | 10 | 10 | 10 | 10 | 10 | 10 |
| Salts of Fatty Acids | | | | | | | | | | |
| Cherries | 0 | 0 | 0 | 0 | 0 | 0 | 0 | 0 | 1 | 2 |
| Blueberries | 0 | 0 | 0 | 0 | 0 | 0 | 0 | 0 | 1 | 2 |
| Grapes | 0 | 0 | 0 | 0 | 0 | 0 | 0 | 0 | 0 | 1 |
| Raspberries | 0 | 0 | 0 | 0 | 0 | 0 | 0 | 0 | 0 | 1 |

*Scale:
0. No visable damage
1. Some browning of leaf veigns, edges and of maturing fruit
5. Approximately 50% of leaves and maturing fruit dessicated
10. All of leaves and maturing fruit dessicated.

The data listed in Table 2 show that the application of dimethyl and methyl anthranilate combined with the solvents and emulsifiers and surfactants disclosed by Kare are toxic to plant tissue. These tests also show that when methyl anthranilate is combined with potassium salts of fatty acids methyl anthranilate no plant toxicity is observed at the concentration rates needed to reduce or eliminate bird depredation on treated surfaces or agricultural crops.

EXAMPLE 3

Tests showing the effect of light on methyl anthranilate and methyl anthranilate mixed with synthetic surfactants such as "Tween"

Two series of uncovered petri dishes, each containing the same amount of solution, were placed in a controlled environment chamber, at 28° C., with incandescent, florescent and ultraviolet lights. Series 1 contained equal amounts of 99.9% pure methyl anthranilate. Series 2 contain equal amounts of methyl anthranilate mixed with Tween in a 1:4 volume ratio. Samples from each series were withdrawn at progressively longer lengths of time, beginning 0.5 hours (h) after first exposure to the light source, and continuing thereafter at twice the preceding time (0.5 h, 1 h, 2 h, 4 h, 8 h, 16 h, 32 h and 64 h).

Each sample was analyzed with a flame reduction gas chromatograph, compared with the known compound, and validated with a mass spectrometer. At the end of 32 hours, less than 10% of the original methyl anthranilate remained and less than 2% of the methyl anthranilate mixed with Tween was present. By the end of 64 hours, only slight traces of methyl anthranilate were found while no traces of methyl anthranilate mixed with Tween could be detected with either instrument. The results of this series of experiments are illustrated in FIG. 1, where bars 10 illustrate use of methyl anthranilate alone and bars 11 show its use when combined with Tween.

The results show diagrammatically in FIG. 1 that methyl anthranilate is subject to degradation under light. The results further demonstrate that mixing the methyl anthranilate with a non-ionic long-chain fatty acid containing 20+ complex carbon molecules, such as "Tween", does not protect the methyl anthranilate or retard the light induced deterioration process.

EXAMPLE 4

Tests showing the effect of potassium salts of fatty acids on prolonging the useful life of methyl anthranilate when exposed to sunlight Five series of petri dishes containing either methyl anthranilate or a mixture of methyl anthranilate and potassium salts of fatty acids were placed in direct sunlight, or in the shade, in the out-of-doors. Series 1, 2 and 3 contained 99.9% methyl anthranilate. Series 4 and 5 contained mixtures of methyl anthranilate and potassium salts of fatty acids, in a 1:4 volume to volume (v/v) ratio. Series 1, and 4 were placed in direct sunlight without glass covers. Series 2 was protected by a glass cover and placed in direct sunlight. Series 3 and 5 were placed, uncovered, in the shade.

Figure 2:
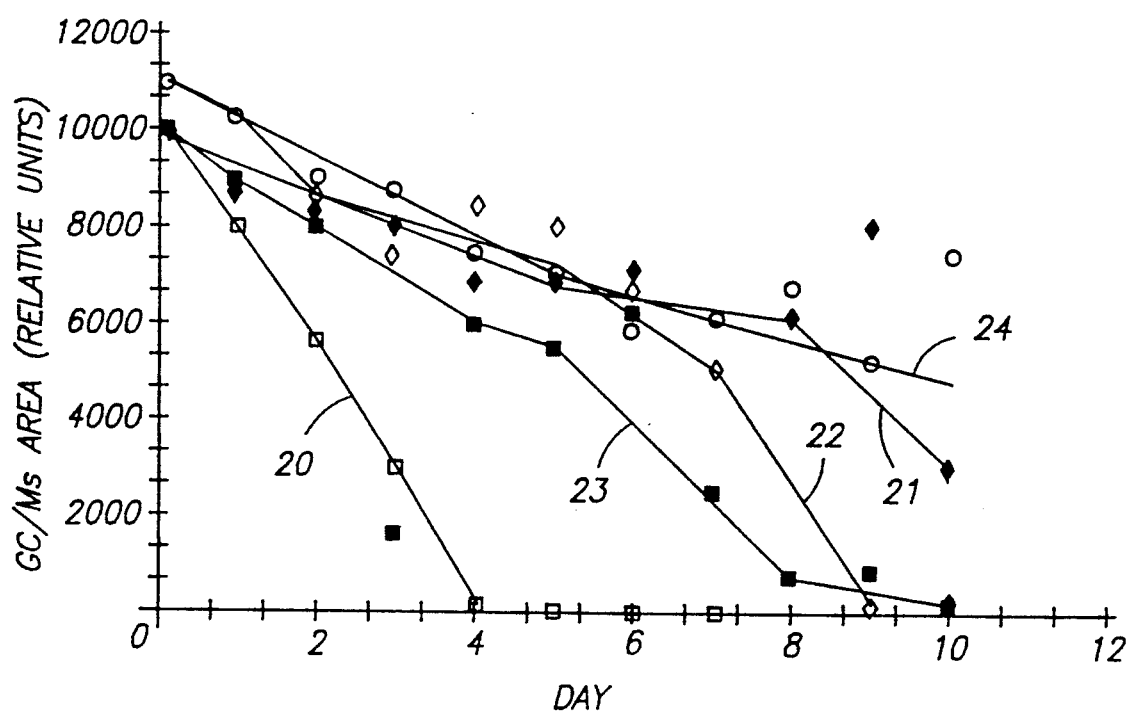
FIG. 2 is a plot of test results showing the effect of shade, glass and potassium salts of fatty acids on the degradation of methyl anthranilate exposed to sunlight.

Samples from each series were collected every 24 hours, processed and analyzed, as in the above example, for remaining methyl anthranilate for ten days. The comparative results are plotted by the five corresponding lines illustrated in FIG. 2 as follows:

Line 20 illustrates the observation of methyl anthranilate (Ma) in Series 1 when exposed to direct sunlight. No residues were detected after day 4.

Line 21 illustrates the observation of methyl anthranilate (Ma) in Series 2 when exposed to sunlight under glass. Residues were detected after 10 days. This confirms the prior study (Example 3) that methyl anthranilate decomposes when exposed to ultraviolet (uv) light since uv light cannot pass through glass.

Line 22 illustrates the observation of methyl anthranilate (Ma) in Series 3 when placed under shade. Residues were detected through day 9. This confirms the volatility of Ma under ambient air conditions and reinforces both the prior study (Example 3) and the data from Series 2 that methyl anthranilate decomposes under uv light.

Line 23 illustrates the observation of methyl anthranilate (Ma) and potassium salts of fatty acids (Fa) in Series 4 when exposed to direct sunlight. Residues were detected through day 10. These data show that the fatty acids retard the degradation of methyl anthranilate under uv light.

Line 24 illustrates the observation of methyl anthranilate (Ma) and potassium salts of fatty acids (Fa) in Series 5 when placed in the shade. Approximately one-half of the original Ma was detected after a 10 day exposure. These data confirm those of Series 2, 3 and 4 and show that volatility of the Ma under ambient air conditions is reduced when combined with Fa.

The results of all these tests demonstrate that methyl anthranilate decomposes when exposed to direct sunlight (Series 1, 2 and 3). Mixing methyl anthranilate with potassium salts of fatty acids protects the methyl anthranilate from sunlight degradation (Series 4 and 5). Methyl anthranilate mixed with fatty acids lasted 2½ times as long as methyl anthranilate alone (Series 1 and 4) when both were exposed to direct sunlight. Methyl anthranilate mixed with fatty acids lasted longer, when placed in the shade than the methyl anthranilate in the glass covered dishes placed in the sun (Series 2 and 5) confirming that the fatty acids form a substantial bond with the methyl anthranilate.

EXAMPLE 5

Tests were conducted to establish the effect of odor as a repellent factor on reducing depredation of bird edibles and other surfaces Three series of trials were developed, using different food sources and caged birds. In Series 1 two feeding trays containing either cherries or grapes were placed in the aviaries each morning. Neither of the food sources in either pan were treated with repellents for one week prior to the test period to acquaint the birds with the food source.

During the test period the food in one set of pans was treated with either dimethyl anthranilate or methyl anthranilate and fatty acids. The second set of pans were left untreated. At the end of four hours all feeding trays were removed and the contents weighed. The results indicate that there were no differences in the repellent characteristics between dimethyl or methyl anthranilate. All of the untreated foods were consumed. Less than 1% of the treated cherries or grapes were consumed. This procedure was repeated for five days with no significant changes noted in the results.

In Series 2 branches of cherries and blueberries were brought directly from the field and placed in the aviaries each morning. As before neither food source were treated with the repellent compound for one week prior to the test period. During the test period one set of branches was left untreated while the other set was treated with methyl anthranilate and potassium salts of fatty acids. On the first day birds began by feeding on both treated and untreated fruit in equal numbers.

Within a few minutes feeding transferred from the treated fruit to the untreated fruit. On the second, and subsequent days when new material was introduced into the aviary, the birds flew to and immediately began eating the untreated fruit even when the location of each sample was rotated. None of the treated fruit was consumed.

Figure 3:
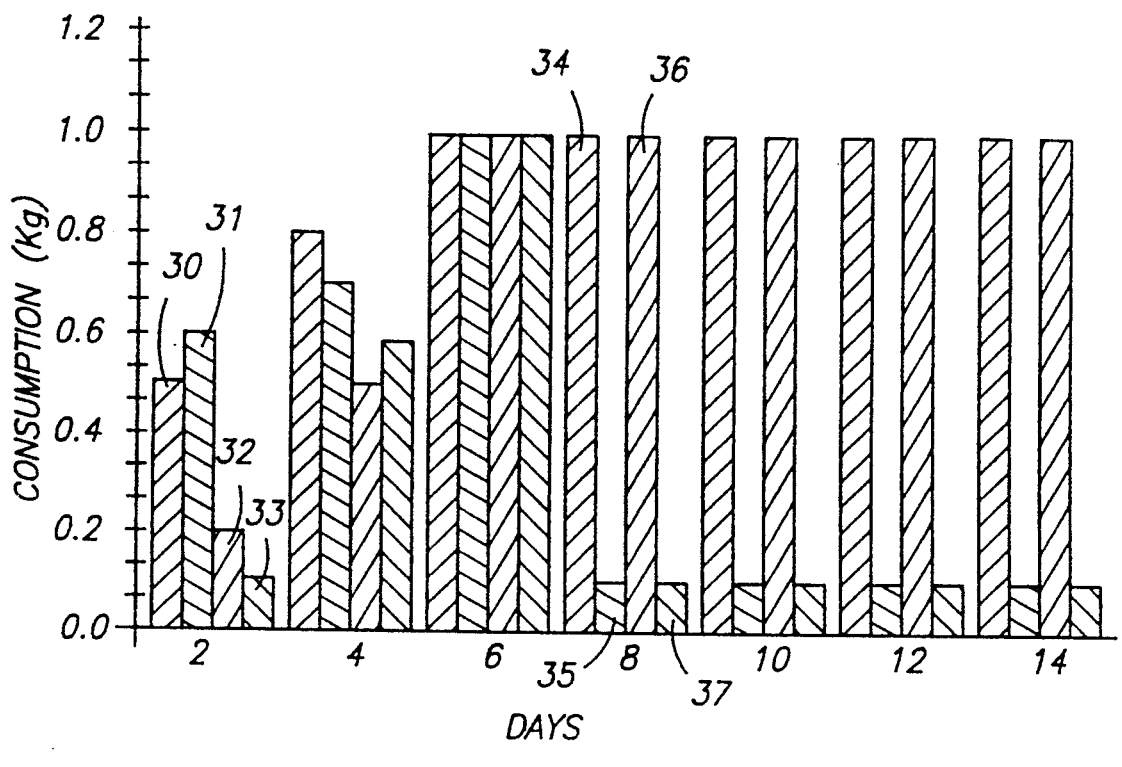
FIG. 3 is a graph summarizing the effectiveness of methyl anthranilate in a mixture of potassium salts of fatty acids in reducing bird depredation on planting seed.

In Series 3, the procedures of Series 1 were repeated with wild pheasants (*Phasianus colchicus*) in the out-of-doors. Resulting consumption patterns are shown in FIG. 3. Untreated wheat and a standard bird mix were provided in four pans and placed side-by-side in an open field. Consumption was recorded for one week. Consumption of the untreated bird mix within two of the pans during the initial seven day Pre-treatment conditioning period is illustrated by bars 30 and 31. Consumption of the wheat is shown by bars 32 and 33. On the 8th day one pan of wheat and one pan of bird mix were treated with methyl anthranilate and fatty acids while the wheat and bird mix in the other pans remained untreated. The contents of each pan were weighed and refilled, as needed, at 24 hour intervals.

Consumption of the untreated (control) bird mix is illustrated by bars 34, while consumption of the treated bird mix is shown by bars 35. Similarly, consumption of control and treated wheat is illustrated by bars 36 and 37, respectively. At the end of the pretreatment period (7 days) the pheasants were consuming approximately one kilogram (2.2 lbs.) of both food sources each day. When the treated materials were introduced consumption immediately dropped to less than 10 g (⅓ oz.) for the following 7 days.

Figure 4:
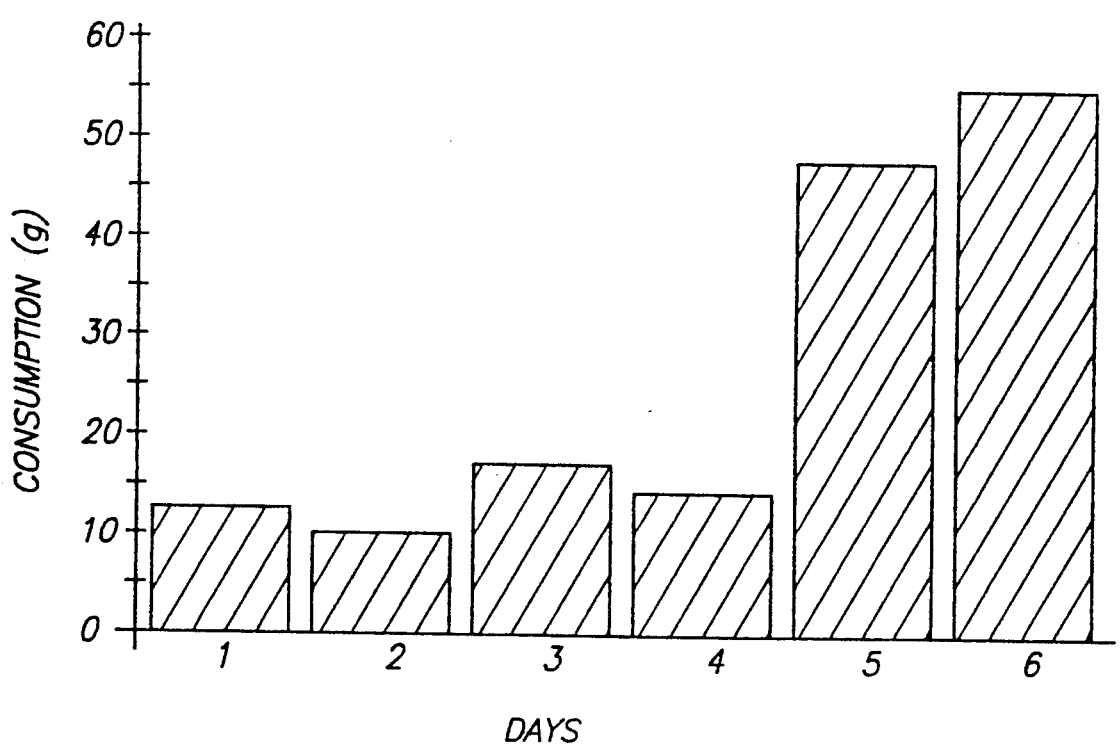
FIG. 4 is a graph summarizing the effectiveness of odor on reducing the consumption of wheat by Pheasants in the presence of methyl anthranilate.

In Series 4 untreated wheat was piled on wire screens placed over the contents of the pans treated with methyl anthranilate and potassium salts of fatty acids (see FIG. 4). As before the pans were randomly placed within the treatment area so that the birds would not associate the treatment with a specific location. The contents placed on the screens were weighed at 24 hour intervals and replaced as necessary.

At the end of this trial period consumption of the untreated wheat placed over the untreated wheat in the pans remained at the 1.0 kilogram level as in Series 4. The consumption of the untreated wheat placed over the treated wheat remained under 20 grams for 4 days, increased to approximately 50 grams on the 5th day and ended with approximately 55 grams on the 6th and last day.

The results of these trials show that there is no difference in the repellency effect between dimethyl and methyl anthranilate on two bird edibles and that the presence of the associated odor, fragrance, aroma or smell reinforced by the aversive taste during initial feeding is a major contributor to the repellency action during the active life of the anthranilates when applied to materials or surfaces to be protected by birds.

EXAMPLE 6

Tests comparing the effectiveness of methyl anthranilate combined with a synthetic emulsifier and methyl anthranilate combined with potassium salts of fatty acids in reducing bird depredation of Early Variety and Bing cherries Two standard solutions of bird repellent formulations were prepared. In the first methyl anthranilate was combined with "Tween (20)", in a 1:4 v/v ratio. In the second methyl anthranilate was combined with potassium salts of fatty acids in a 1:4 v/v ratio. Both were diluted to a 1.0% solution in water and applied to randomly selected trees within two ripening cherry orchards. Pre- and post-treatment samples were collected by counting the number of whole and damaged fruit at various locations within the canopies of both treated and untreated trees.

Figure 5:
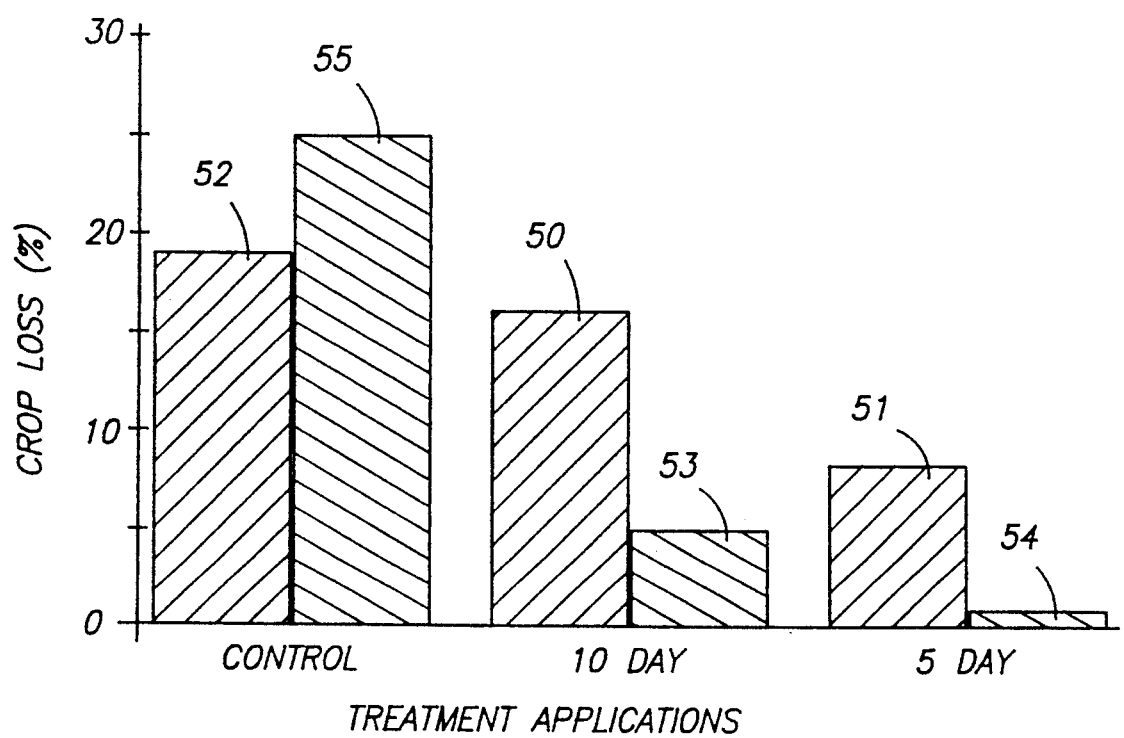
FIG. 5 is a graph summarizing the effectiveness of methyl anthranilate in a mixture of potassium salts of fatty acids in reducing bird depredation on cherries.

The Early Varietal test cultivars were treated with the Kare formulation (first formulation of methyl anthranilate and Tween). Three trees within the block were treated once. Three additional trees within the same block were treated twice at five day intervals. Both treatments were compared with four untreated trees. The resulting consumption patterns are shown in FIG. 5 by bars 50, 51 and 52, respectively.

In the second orchard four Bing cherry trees were treated twice at ten day intervals with the second formulation. Another three Bing cherry trees within the same block were treated three times at five day intervals with the second formulation. Both treatments began at the "straw" coloration stage (when sugars are first accumulated) and ended when the fruit had fully matured.

All samples were compared with three nontreated trees from within the same orchard. The resulting consumption patterns are shown in FIG. 5 by bars 53, 54 and 55, respectively.

When applied to cherries, depredation by robins (*Turdus migratorius*) was reduced 13% with only one application of the repellent and 55% with two applications during the last ten days of the ripening process in the Early Varieties with the methyl anthranilate and Tween formulations. When applied to the Bings when they were beginning to ripen, damage was reduced approximately 76% with the 10 day treatments and over 97% with the 5 day treatments (FIG. 5) with the methyl anthranilate and soap.

These results show that methyl anthranilate is only marginally effective when applied to a crop with surfactants such as "Tween." When formulated with potassium salts of fatty acids the efficacy of the methyl anthranilate is greatly enhanced and becomes a practical solution under commercial agricultural settings.

EXAMPLE 7

Tests for methyl anthranilate residues in Early Variety cherries

Methyl anthranilate was combined with potassium salts of fatty acids, in a 1:4 v/v ratio, and diluted to a 1.0% solution in water. This formulation was then applied to six randomly selected trees within a ripening cherry orchard.

Cherries were randomly collected each day, for 10 days, from each of the treated trees, washed in solvent, and the amount of residual methyl anthranilate on the fruit measured with a gas chromatograph, verified with a gas chromatograph, and compared with comparable untreated samples. The results show that there was a gradual reduction in the amount of methyl anthranilate present on the fruit during the 10 day period. At the end of the treatment period no methyl anthranilate was detected on either the treated or untreated samples.

This experiment shows that methyl anthranilate, when combined with potassium salts of fatty acids and applied to a maturing fruit crop, gradually decomposes and does not leave any detectable residues on the harvested fruit.

EXAMPLE 8

Tests for the effectiveness of methyl anthranilate solutions in potassium salts of fatty acids solution in reducing bird depredation of highbush blueberries In this series of trials a repellent formulation, consisting of methyl anthranilate and potassium salts of fatty acids in a 1:4 v/v ratio and diluted with water to form a 1.0% solution, was applied to ripening Highbush Pemberton and Jersey blueberries with a history of bird depredation.

Six rows within each variety were selected for the trial. Four plants in each of two rows were either covered with netting to exclude the birds, left unnetted and untreated, or treated with the repellent formulation. Treatment of the designated plants was initiated one week prior to the first harvest and continued at seven day intervals until all of the crop had been removed from the field. All of the ripe berries from each plant within the research plot were harvested, weighted and recorded at seven day intervals.

Figure 6:
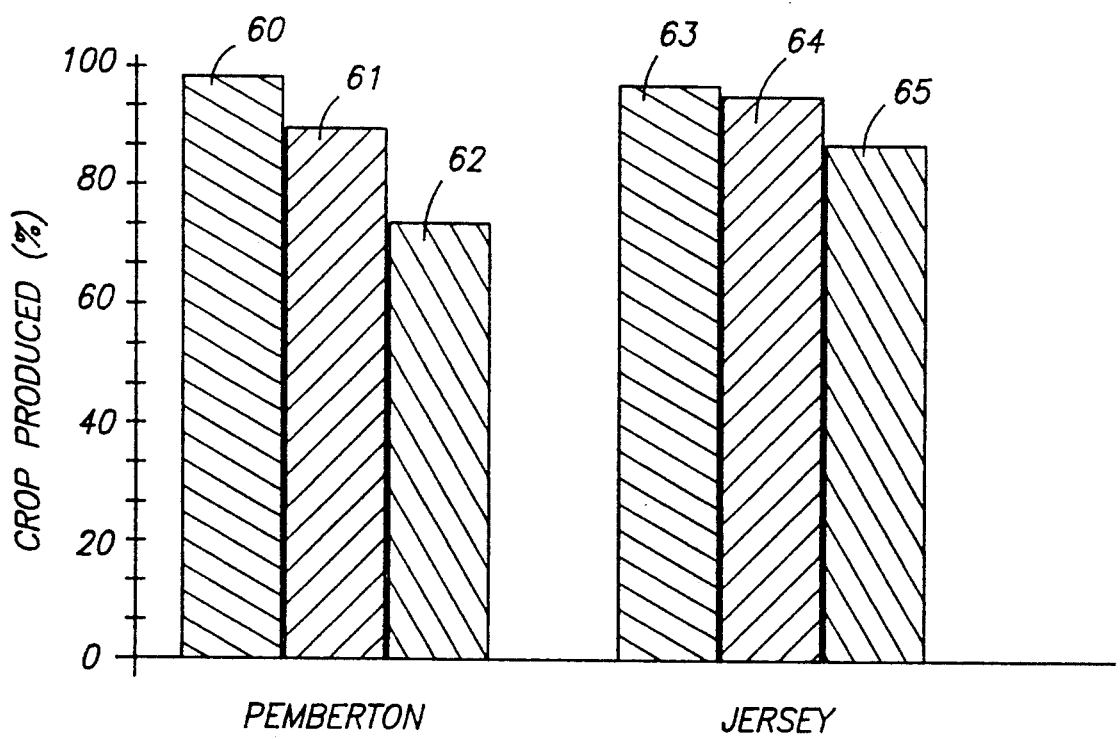
FIG. 6 is a graph summarizing the effectiveness of methyl anthranilate in a mixture of potassium salts of fatty acids in reducing bird depredation on blueberries.

The results of these trials show that methyl anthranilate, when combined with potassium salts of fatty acids, is effective in reducing bird depredation to blueberries. Crop production results, shown in FIG. 6, are based upon the netted plants (bar 60—Pemberton plants; bar 63—Jersey plants). Damage to the Pemberton's was reduced approximately 64% when the crop produced on the treated plants (bar 61) were compared with the untreated and unnetted controls (bar 62). Damage to the Jersies was almost completely eliminated (damage reduction=99.9%). No significant differences in the total amount of blueberries produced by the treated plants (bar 64) and the netted controls could be detected with standard statistical analysis (FIG. 6). The decrease in crop production observed in the untreated and unnetted control plants is shown by bar 65.

These results show that the consistent application of methyl anthranilate, combined with potassium salts of fatty acids, reduces or eliminates bird depredation of blueberries.

EXAMPLE 9

Tests for taste residues were conducted on human subjects with two varieties of cherries and highbush blueberries Methyl anthranilate was combined with potassium salts of fatty acids, in a 1:4 v/v ratio, diluted to a 1.0% solution in water and applied to Early Varietal and Bing cherries as well as Pemberton and Jersey Highbush blueberries. Samples from both treated and untreated plants were harvested, six days after the last treatment, and given to twenty volunteer subjects to taste. Each subject was provided two treated and one untreated samples and two untreated and one treated samples on two separate plates.

Each sample was identified with a randomly generated number. Each subject was asked to "identify the odd tasting sample" and record their answer. None of the test subjects were able to detect any methyl anthranilate residues in the samples.

EXAMPLE 10

Wine grapes were examined for bird depredation

Methyl anthranilate was combined with potassium salts of fatty acids, in a 1:4 v/v ratio, diluted to a 2.0% solution in water, and applied to Gewurtztraminer, Semillon and Limber grapes. One treatment was made 12 days prior to anticipated harvest. Bird predation on the crops was assessed prior to the treatment and at harvest by removing randomly selected clusters of grapes, counting missing or partially eaten fruits, and recording the percentage of missing or damaged fruit.

Six rows of mature vines, within each variety, were selected for the study. Two rows of vines were sprayed with the repellent compound. Two rows were not treated. Two rows were used as a buffer strip between the treated and untreated samples.

Figure 7:
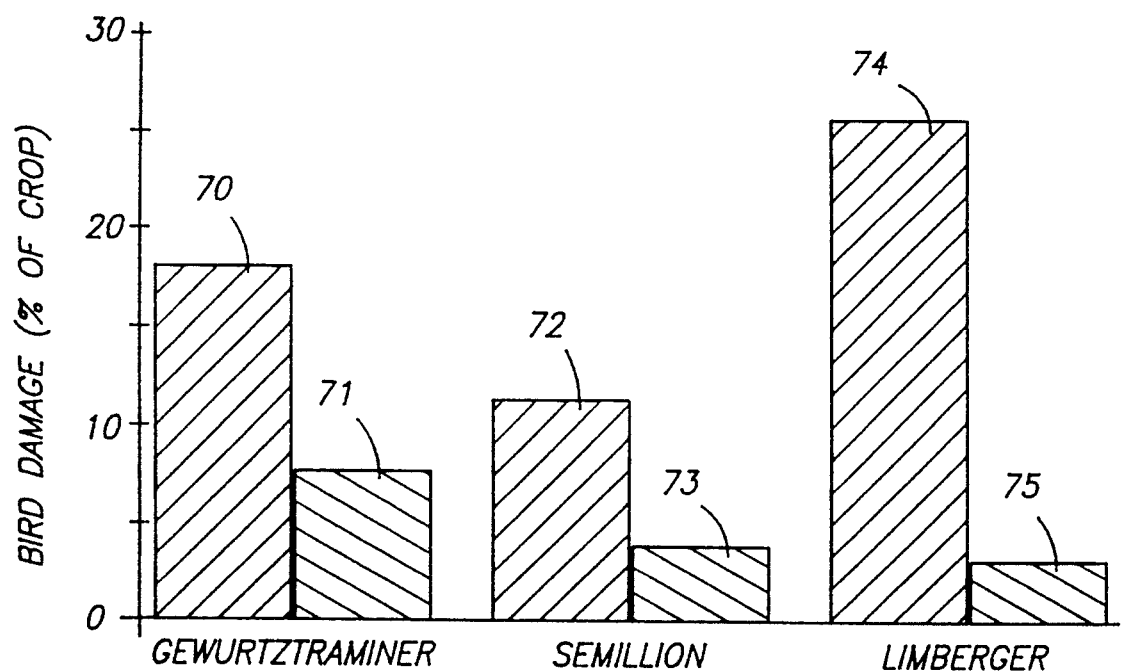
FIG. 7 is a graph summarizing the effectiveness of methyl anthranilate in a mixture of potassium salts of fatty acids in reducing bird depredation of Gewurtztraminer, Semillon and Limberger grapes.

As shown in FIG. 7, it was found that bird damage to the treated crops decreased 58.17% for Gewurtztraminer, 64.33% for Semillon and 88.3% for Limberger grapes when the treated plots (bars 71, 73 and 75, respectively) were compared with the untreated controls (bars 70, 72 and 74, respectively) at harvest. These results show that 0.5% methyl anthranilate in a 1.0% solution of potassium salts of fatty acids (by volume) will significantly reduce bird depredation on the types of grapes tested.

EXAMPLE 11

Tests were conducted on the repellent's efficacy when applied to perches

Two perches were established in a 10×15 ft outdoor aviary and their use by starlings recorded for 30 days. Methyl anthranilate and potassium salts of fatty acids, in a ratio of 1:4, was applied to the most frequently used perch with a paint brush and the bird's reactions observed for 7 days.

Immediately after application the birds flew to the perch, began ruffling their feathers, flapping their wings and rubbing their beaks. Within one minute activity was confined to the untreated perch, ground foraging and washing in water. Twice each day, for 8 days, attempts were made to force the birds to use the treated perch by scaring them from the untreated perch. When forced from the untreated perch during the first 5 days the birds would fly toward the treated perch, change their flight pattern, and either attempt to return to the untreated perch or land on the ground until the disturbance was terminated.

On days 6 and 7 the birds began landing on the perch but continued to show the signs of stress noted on their initial contact with the treated perch during day 1. During the remainder of the day, in the absence of any disturbance, use was confined to the untreated perches or ground. By day 8 perch use within the aviary returned to that observed during the 30 day pre-treatment period.

The results show that the presence of the methyl anthranilate odor is sufficient to repel birds from perch use. Further, that the anthranilitic odor is the most important factor in the compound's repellency characteristics.

EXAMPLE 12

Tests were conducted on the repellent's efficacy on interrupting nest building activity Methyl anthranilate and potassium salts of fatty acids, in a v/v ratio of 1:4, were applied with a paint brush to swallow nests being built under the eaves of a house and the birds' reactions observed for 7 days. Upon initial contact with the newly treated nests the birds began flying around in circles, making loud noises, and exhibiting confusion. The birds continued to circle the area, during the next 10 hours, but aborted each landing before touching the nests. After 38 hours all nest building attempts had been terminated and were not reinitiated for the remainder of the 7 day observation period.

This test demonstrates that the methyl anthranilate odor, fragrance, aroma or smell is sufficient to repel birds from areas to be protected even after becoming habituated to the site.

EXAMPLE 13

Tests were conducted in the repellent's efficacy on a water source

Fresh water in a container was placed daily in a 10×15 ft outdoor aviary and its use by starlings was recorded for 30 days.

In the first trial one container of water treated with a 4% solution of methyl anthranilate and potassium salts of fatty acids was placed in the aviary for one hour after an untreated container of water had been removed for two hours. Initial watering attempts, by the birds, were followed by repeated bill wiping to remove the material from the beak, wing flapping and feather ruffling; all considered stress symptoms by avian biologists. During subsequent watering attempts the birds would fly to the container, perch but leave before drinking. Upon removal of the treated water and the introduction of untreated fresh water, the birds immediately drank from and bathed in the untreated water container.

In the second trial two fresh water sources were provided each day to starlings with no prior exposure to the repellent compounds and their behavior recorded for a 10 day period. On day 1 of the trial one container of treated water, containing 4% methyl anthranilate and potassium salts of fatty acids in a 1:4 v/v mixture, and one container of untreated water were placed in the aviary after all of the water had been removed for two hours.

Upon placement of both water sources in the aviary approximately equal numbers of birds flew to each container. Those drinking from the untreated water source exhibited no behavioral changes from that noted during the pre-treatment period. The remainder, within one minute upon contact with the treated water source, began rubbing their beaks on the side of the container, flapping their wings and ruffling their feathers; all signs of physical distress. Each then flew to the untreated container of water, immersed their heads and washed their feathers for several minutes.

During the following 7 day period none of the birds were observed using or perching on the treated water containers. On day 9 the birds began using the treated and untreated water sources. By day 10 both water sources were used at approximately equal frequencies.

The results of trial one indicate that the birds will not use water treated with methyl anthranilate and potassium salts of fatty acids when deprived for two hours. The results of trial two indicate that the associated odor reinforces the birds' aversion to the treated material and is sufficient to repel bird use of the material until the presence of the methyl anthranilate is removed.

EXAMPLE 14

Tests for the effectiveness of methyl anthranilate and potassium salts of fatty acids in reducing bird depredation of planting seed Twenty ml. of methyl anthranilate was added to eighty ml. aqueous solution of potassium salts of fatty acids and mixed with milo, sunflower and wheat seed. Three sets of two feeding stations were placed on top of the snow, in the out-of-doors, where pheasants were known to congregate and feed.

During the 5 day pretreatment phase of the trial, 2 kg. of untreated seed from each species was placed in the pans to acquaint the birds with each food source and determine total consumption. On day 6 two kg. of each treated seed were placed in one set of pans with a like amount placed in a second set of pans (controls).

During the pretreatment and treatment phases of the trial the contents of each pan were removed, weighted, recorded and replaced with a new supply of seed. The amount of seed eaten from the treated samples was then compared with that eaten from the controls during the treatment period and the pre-treatment period.

The results of the experiment showed that the amount of seed consumed by the birds was reduced with one application of methyl anthranilate and potassium salts of fatty acid solution compared with the seed that had not been treated (FIG. 3).

Sub-samples from each variety were wrapped in moist towels and placed under refrigeration at 1.0% C for 7 days. Differences in germination rates were then calculated by comparing the untreated with the treated seed. The results show that the seed treated with the methyl anthranilate and potassium salts of fatty acid solutions germinated as well as the untreated seed.

EXAMPLE 15

Tests were conducted on the effect of adding potassium salts of fatty acids to methyl anthranilate to inhibit insect attractiveness Two series of six petri dishes containing either methyl anthranilate and ethanol (95%) or methyl anthranilate and potassium salts of fatty acids in a 1:4 v/v ratio were placed in a cherry orchard and exposed for three days.

At the end of the trial period the number of insects adhering to the residual film in the dishes were identified and counted. Twenty fruit flies (*Chloropidae thaumatomya glabra*) were collected from the six dishes containing the methyl anthranilate and ethanol. None were found on the petri dishes containing methyl anthranilate and potassium salts of fatty acids.

This test demonstrates that the addition of potassium salts of fatty acids inhibits the attractiveness of the methyl anthranilate to insects.

SUMMARY

The compositions of this invention, combining known repellents and an anionic surfactant or emulsifier agent, such as salts of fatty acids, reduce avian depredation by providing repellent characteristics that have additional important and unexpected advantages over the same bird repellents in formulations previously disclosed. The water insoluble repellent compounds have been discovered to be dispersible in aqueous solutions when combined with metal salts of fatty acid components; natural soaps. This unique formulation facilitates applications to surfaces of plants and other materials to be protected from bird damage, consumption or use without damaging them in higher concentrations than previously recorded.

The compositions may be formulated as a concentrate or ready-to-use solution which is not toxic to humans, birds and other wildlife, or plants. The addition of metal salts of fatty acids also have the unexpected result of protecting the repellents from ultraviolet light and weathering. This increases the useful lifespan of the material when applied to a crop or surface in the out-of-doors.

It has also been discovered, and documented within the body of this disclosure, that the fragrance or aroma dissipated during the volatilization process is the most important component of the anthranilates that repels the birds and is reinforced by the aversive taste of the repellent compounds. In the presence of these fragrances or aromas repeated entry into the protected or treated area is reduced or eliminated. It was also discovered that the addition of soap to the repellent reduces or eliminates phytotoxicity, extends the useful life of the repellent under sunlight and reduces the attractiveness of the latter to insects.

The problems preventing wide-spread use of the repellent compounds in the past have been solved by this invention.

In compliance with the statute the invention has been described in language more or less specific as to structural features. It is to be understood, however, that the invention is not limited to the specific features shown since the means and construction herein disclosed comprise a preferred form of putting the invention into effect. The invention is, therefore, claimed in any of its forms or modifications within the proper scope of the appended claims appropriately interpreted in accordance with the doctrine of equivalents.

I claim:

1. A bird repellent composition for protecting agricultural crops, aquatic systems, and man-made structures from avian depredation, damage or use, consisting of a mixture of:
   (a) a chemical repellent consisting of a benzoic derivative of esters of anthranilic acid, phenylacetic acid or dimethyl benzyl carbonyl acetate having repellent affects, through smell and taste, on birds; and
   (b) at least one anionic surfactant or emulsifier consisting of a saturated or unsaturated alkyl metal salt of a fatty acid having a chain length of 10 to 22 carbons and being formulated with carboxylic acids and salts thereof, phosphoric and polyphosphoric acid esters and salts thereof, sulfonic acids and salts thereof, sulfuric acid esters and salts thereof, sulfated esters or sulfated natural fats and oils that is a derivative of hydrogen, potassium, sodium, lithium, rubidium, cesium or francium;
   the weight or volume ratio of the chemical repellent to the anionic surfactant or emulsifier agent being between 5:1 and 1:20;
   the mixture further including water mixed with the chemical repellent and the anionic surfactant or emulsifier agent to produce an evenly distributed aqueous solution having a 0.01% to 40% concentration of the chemical repellent by weight or volume with no precipitation;
   wherein a bridge is formed by the anionic surfactant or emulsifier that separates the chemical repellent in water and from surfaces to which the mixture is applied.

2. The bird repellent composition of claim 1 wherein the chemical repellent is methyl anthranilate.

3. The bird repellent composition of claim 1 wherein the chemical repellent is dimethyl anthranilate.

4. The bird repellent composition of claim 1 wherein the anionic surfactant or emulsifier agent is a derivative of potassium.

5. The bird repellent composition of claim 1 wherein the anionic surfactant or emulsifier agent is a derivative of sodium.

6. The bird repellent composition of claim 1 wherein the weight or volume ratio of the chemical repellent to the anionic surfactant or emulsifier agent is between 1:1 and 1:4.

* * * * *